United States Patent
Waiblinger et al.

(10) Patent No.: US 9,431,212 B2
(45) Date of Patent: Aug. 30, 2016

(54) METHOD FOR DETERMINING THE PERFORMANCE OF A PHOTOLITHOGRAPHIC MASK

(75) Inventors: Markus Waiblinger, Constance (DE); Michael Budach, Hanau (DE); Thomas Scherübl, Jena (DE); Dirk Beyer, Weimar (DE)

(73) Assignee: Carl Zeiss SMS GmbH, Jena (DE)

( * ) Notice: Subject to any disclaimer, the term of this patent is extended or adjusted under 35 U.S.C. 154(b) by 0 days.

(21) Appl. No.: 13/701,286

(22) PCT Filed: Apr. 29, 2011

(86) PCT No.: PCT/EP2011/056869
§ 371 (c)(1),
(2), (4) Date: Feb. 5, 2013

(87) PCT Pub. No.: WO2011/151116
PCT Pub. Date: Dec. 8, 2011

(65) Prior Publication Data
US 2013/0126728 A1 May 23, 2013

Related U.S. Application Data

(60) Provisional application No. 61/351,056, filed on Jun. 3, 2010.

(51) Int. Cl.
*G01N 23/00* (2006.01)
*H01J 37/28* (2006.01)
(Continued)

(52) U.S. Cl.
CPC ........... *H01J 37/28* (2013.01); *G01N 23/2208* (2013.01); *G01N 23/2251* (2013.01); *G03F 1/86* (2013.01); *G01N 2223/072* (2013.01); *G01N 2223/079* (2013.01); *G03F 1/24* (2013.01)

(58) Field of Classification Search
CPC .......... H01J 37/00; H01J 37/02; H01J 37/21; H01J 37/22; H01J 37/24; H01J 37/244; H01J 37/26; H01J 37/261
USPC ................................ 250/306, 307, 310, 311
See application file for complete search history.

(56) References Cited

U.S. PATENT DOCUMENTS

| 5,717,204 A * | 2/1998 | Meisburger et al. ......... 250/310 |
| 2002/0070340 A1* | 6/2002 | Veneklasen et al. ......... 250/310 |

(Continued)

FOREIGN PATENT DOCUMENTS

| EP | 0628806 A2 | 12/1994 |
| EP | 1829052 B1 | 4/2008 |

(Continued)

OTHER PUBLICATIONS

Ludwig Reimer, "Scanning Electron Microscopy: Physics of Image Formation and Microanalysis (Springer Series in Optical Sciences)", 2nd (second) completely rev edition by Reimer, Ludwig published by Springer (1998), pp. 101-106; 138-142; and 148-152.

(Continued)

*Primary Examiner* — Jason McCormack
(74) *Attorney, Agent, or Firm* — Fish & Richardson P.C.

(57) ABSTRACT

The invention relates to a method for determining a performance of a photolithographic mask at an exposure wavelength with the steps of scanning at least one electron beam across at least one portion of the photolithographic mask, measuring signals generated by the at least one electron beam interacting with the at least one portion of the photolithographic mask, and determining the performance of the at least one portion of the photolithographic mask at the exposure wavelength based on the measured signals.

21 Claims, 13 Drawing Sheets

(51) Int. Cl.
*G01N 23/22* (2006.01)
*G01N 23/225* (2006.01)
*G03F 1/86* (2012.01)
*G03F 1/24* (2012.01)

(56) References Cited

U.S. PATENT DOCUMENTS

| | | | |
|---|---|---|---|
| 2005/0185173 A1* | 8/2005 | Hau-Riege | B82Y 10/00 356/237.5 |
| 2006/0082763 A1* | 4/2006 | Teh et al. | G01N 21/9501 356/72 |
| 2007/0194231 A1* | 8/2007 | Nakahira | H01J 37/28 250/310 |
| 2007/0288219 A1* | 12/2007 | Zafar | G03F 1/84 703/14 |
| 2008/0099674 A1* | 5/2008 | Bihr | G03F 1/72 250/307 |
| 2008/0197280 A1* | 8/2008 | Tanaka et al. | 250/306 |
| 2009/0152460 A1* | 6/2009 | Buhler et al. | 250/306 |
| 2009/0152461 A1* | 6/2009 | Kim | H01J 37/244 250/307 |
| 2009/0278923 A1 | 11/2009 | Endo | |
| 2009/0317732 A1 | 12/2009 | Itoh et al. | |
| 2010/0019147 A1* | 1/2010 | Hatakeyama | G03F 1/0092 250/307 |
| 2010/0112464 A1 | 5/2010 | Kanamitsu | |
| 2010/0203432 A1* | 8/2010 | Itoh | 430/5 |
| 2010/0233594 A1* | 9/2010 | Zhang | 430/5 |
| 2010/0237256 A1* | 9/2010 | Yoshitake | 250/491.1 |

FOREIGN PATENT DOCUMENTS

| | | | |
|---|---|---|---|
| JP | 63-266754 | 11/1988 | H01J 37/28 |
| JP | 2009-270976 | 11/2009 | G01N 21/956 |
| JP | 2010-002772 | 1/2010 | G03F 1/08 |
| JP | 2010-025788 | 2/2010 | G01N 23/225 |
| JP | 2010-109164 | 5/2010 | H01L 21/027 |
| WO | 03071578 A2 | 8/2003 | |

OTHER PUBLICATIONS

Japanese Office Action with English translation, Application No. 2013-521805, by Examiner of the Patent Office Hiroki Sano, dated Dec. 25, 2013 (6 pages).

English translation of Office Action for Taiwan Patent Application No. 100119555 dated Feb. 25, 2015 (5 pages).

* cited by examiner

Fig. 13
(a)
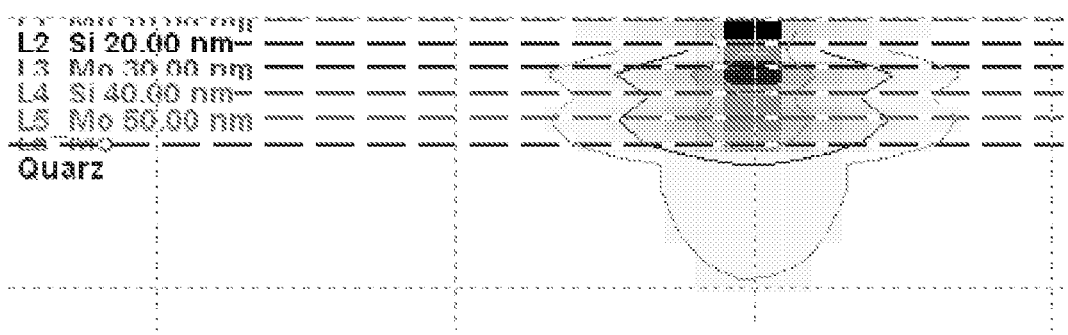
(b)
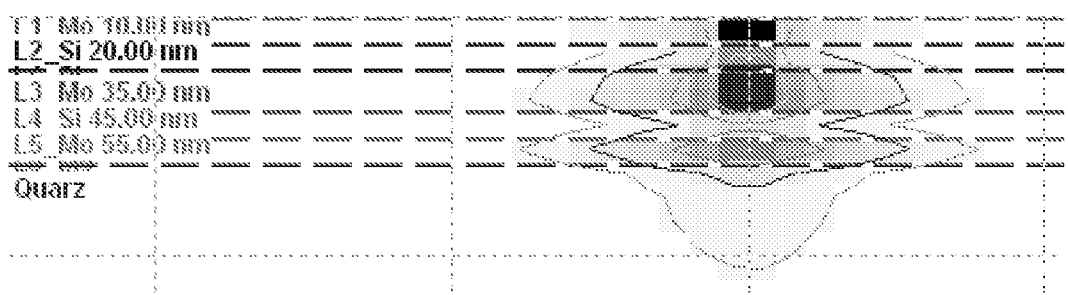

METHOD FOR DETERMINING THE PERFORMANCE OF A PHOTOLITHOGRAPHIC MASK

CROSS-REFERENCE TO RELATED APPLICATIONS

This application is a national stage application of PCT/EP2011/056869, filed on Apr. 29, 2011, which claims priority to U.S. Provisional Application 61/351,056, filed on Jun. 3, 2010, herein incorporated by reference in its entirety.

1. TECHNICAL FIELD

The present invention relates to a method and an apparatus to determine the performance of a photolithographic mask.

2. PRIOR ART

As a result of the constantly increasing integration density in the semiconductor industry, photolithographic masks have to project smaller and smaller structures. In order to fulfil this demand, the exposure wavelength of photolithographic masks has been shifted from the near ultraviolet across the mean ultraviolet into the far ultraviolet region of the electromagnetic spectrum. Presently, a wavelength of 193 nm is typically used for the exposure of the photoresist on wafers. As a consequence, the manufacturing of photolithographic masks with increasing resolution is becoming more and more complex, and thus more and more expensive as well.

Photolithographic masks have to fulfil highest demands with respect to transmission, planarity, pureness and temperature stability. Further, they have to be free of defects, since each defect on a mask may be reproduced on each wafer exposed through this photolithographic mask. However, no manufacturing process can guarantee an absolute freedom from defects. Therefore, each manufactured mask has to be checked or inspected whether a defect on the mask will be transferred to the wafer during the exposure process. As the manufacturing of photolithographic masks is a cost-intensive process, defects on a mask are repaired whenever possible. After the repairing, the photolithographic mask has again to be very carefully checked. An AIMS (Aerial Image Measurement System) system is regularly used for this purpose. The AIMS creates a highly magnified image of the structures the photolithographic mask will create on a wafer at the exposure wavelength. This magnified image is recorded by an UV (ultraviolet) sensitive CCD (charge coupled device) camera. The European patent application EP 0 628 806 A2 discloses the set-up and operation of such an AIMS system.

In the future, the demand to realize smaller and smaller structures on wafers can no longer be fulfilled with photolithographic systems using electromagnetic radiation at a wavelength of 193 nm. Therefore, photolithographic systems are presently developed which will operate in the EUV (extreme ultraviolet) region of the electromagnetic spectrum at a wavelength of 13.5 nm. These photolithographic systems will enable to generate structures on wafers with dimensions of less than 20 nm. The European patent EP 1 829 052 B1 discloses a reflective multi-layer mirror for such a system.

The AIMS systems presently available for the inspection of photolithographic masks can not be used for EUV masks as the present systems operate with lens systems. These lenses are not transparent for electromagnetic radiation at a wavelength of 13.5 nm.

At the moment, an inspection system for EUV photolithographic masks is not available. It is presently not even clear whether such a system will ever be developed as the development costs for such an inspection system are enormous. Moreover, the number of EUV inspection systems required on a world-wide basis is limited. In addition, the operation of such a tool would be very complex and expensive.

On the other hand, due to the reduction of exposure wavelength by more than one order of magnitude (from 193 nm to 13.5 nm) and the new type of photolithographic mask, it will be mandatory to check or inspect each EUV mask prior to its application in a EUV photolithographic system.

The present invention is therefore based on the problem to provide a method and an apparatus for determining the performance of an EUV photolithographic mask that at least partially avoids the above-mentioned disadvantages.

3. SUMMARY OF THE INVENTION

According to a first embodiment of the invention, this problem is solved by a method according to patent claim 1. In an embodiment, a method for determining a performance of a photolithographic mask at an exposure wavelength comprises scanning at least one electron beam across at least one portion of the photolithographic mask, measuring signals generated by the at least one electron beam interacting with the at least one portion of the photolithographic mask, and determining the performance of the at least one portion of the photolithographic mask at the exposure wavelength based on the measured signals.

When an electron beam strikes a sample, electrons are backscattered from and photons are generated in the sample. These backscattered electrons and generated photons carry information specific for the composition of the sample. Consequently, both the electrons and photons generated by the striking electron beam can be used to evaluate or analyse the composition of a sample. For example, by varying the energy of the incident electrons, it is possible to reach different depths within the sample (L. Reiner: "Scanning of electron microscopy", p. 101ff, $2^{nd}$ Edition, October 1998, Springer Verlag). This analysis can be performed since the basic physical laws controlling the interaction of electrons and photons within a sample are well known and understood. Accordingly, these physical laws can also be applied to determine the behaviour of photons of a predetermined wavelength incident on a sample of known composition. Thus, measuring electrons backscattered from a sample will allow predicting the performance of this sample with respect to incident photons of a predetermined wavelength. By scanning an electron beam with a small spot size a sample can be probed with a high spatial resolution.

The application of the method defined in claim 1 avoids the generation of a photon beam and the set-up of a complex optic at the exposure wavelength for the inspection of photolithographic masks. Instead an electron beam of a conventional scanning electron microscope can be used.

In the presently preferred embodiment, electrons are used to scan the photolithographic mask. As already mentioned, an electron beam can be focused to a small spot so that measurement data from the mask can be obtained with a high resolution. Furthermore, electron beams do not have a detrimental effect on the sample to be investigated. Alternatively, photons and/or ions can also be used for scanning the photolithographic mask. It is further conceivable to use a combination of beams of different particles, i.e. electrons and/or photons and/or ions for scanning the photolithographic mask in order to measure signals generated by the particle beam.

The performance of a photolithographic mask is in one aspect defined by the capability of the photolithographic mask to transmit a predetermined the structure or pattern in a photoresist arranged on a wafer essentially without any defects.

In a further aspect of the invention, the method may further comprise scanning the at least one electron beam with multiple beam energies. The size of the interaction volume, in particular its size in the direction of the electron beam, varies with the kinetic energy of the electrons in the electron beam. Therefore, multiple scans with various beam energies across the same portion of the photolithographic mask provide a depth profile of the composition of the portion of the mask.

In an additional aspect, the photolithographic mask may comprise a reflective photolithographic mask. In a further preferred embodiment, the photolithographic mask may comprise a photolithographic mask for an extreme ultraviolet (EUV) exposure wavelength, in particular for a wavelength around 13.5 nm.

Additionally, in a further aspect, measuring signals may comprise measuring of electrons, in particular measuring of backscattered electrons, wherein measuring of backscattered electrons may comprise measuring of a yield of backscattered electrons and/or measuring an energy distribution of backscattered electrons. These quantities are influenced by the composition of the sample.

In a preferred embodiment, measuring signals may comprise measuring of photons, in particular measuring photons using the energy dispersive x-ray spectroscopy (EDX). The energy resolved photon spectrum comprises characteristic x-ray photons which are specific for the composition of the sample.

In a further preferred embodiment, measuring signals may comprise measuring of electrons and measuring of photons, in particular measuring of backscattered electrons and measuring of photons using the energy dispersive x-ray spectroscopy. The simultaneous measurement of electrons and photons facilitate the determination of the composition of complex samples.

In a further aspect, the method may further comprise simulating signals generated by the electron beam interacting with the portion of the photolithographic mask and determining the performance of the portion of the photolithographic mask at the exposure wavelength by evaluating simulated and measured signals. As the basic physical laws controlling the interaction of electrons and photons with the sample are known, the effect of an electron beam incident on a sample may be simulated for a sample with a known composition. Thus, by analyzing measured and simulated data it can be determined whether the measured and simulated samples have an essentially identical composition. Having determined the composition of the sample, the effect of a photon beam incident with a predetermined wavelength on the known sample may also be simulated.

Furthermore, in an additional aspect, the method may further comprise determining a defect in the performance at the exposure wavelength of a portion of the photolithographic mask by analyzing measured signals of different portions of the photolithographic mask and/or by analyzing measured and simulated signals. This means that a defect of a photolithographic mask at the exposure wavelength of EUV photons can be analyzed by using an electron beam. Therefore, the defined method avoids highly complex, time-consuming and expensive wafer prints.

In a further particularly preferred embodiment, the method may further comprise correcting the defect by using the at least one electron beam. This embodiment has the advantage that the defect localization and the repair of the defect can be performed in a single device and, thus significantly reducing the effort and time needed for mask repair.

In a further aspect, the defect is a multi-layer defect of the photolithographic mask which is repaired by a compensational repair of the absorber layer of the photolithographic mask. There are two different kinds of defects on a photolithographic mask. Defects of the absorber layer can occur due to missing absorber material or due to excessive absorber material. Excessive absorber material may be removed by providing a precursor gas acting in combination with the electron beam as an etching gas. Missing absorber material may be deposited by providing a precursor gas which is decomposed by the electron beam and the corresponding component of the precursor gas is locally deposited at the position of missing absorber material. On the other hand, defects in the multi-layer structure of the photolithographic mask can not directly be corrected in the multi-layer structure. Instead, these defects are repaired by a compensational repair of the absorber layer. This means that the absorber layer is modified in such a way that the defect in the multi-layer system is essentially compensated.

In an additional aspect, the method may further comprise using a method according to any one of the preceding embodiments for determining the performance of the repaired portion of the photolithographic mask at the exposure wavelength. After a repair process the mask has to be inspected again. If this can be performed inside the inspection device without requiring a wafer print, the effort of mask manufacturing can considerably be reduced.

In a particularly preferred embodiment, an apparatus for determining a performance of a photolithographic mask at an exposure wavelength may comprise at least one electron source for generating at least one electron beam, at least one adjusting means for scanning the at least one electron beam across the at least one portion of the photolithographic mask, at least one detector for measuring signals generated by the at least one electron beam interacting with the at least one portion of the photolithographic mask, and at least one computing means for determining the performance of the at least one portion of the photolithographic mask at the exposure wavelength based on the measured signals.

Scanning electron microscopes are mature devices, whereas sources for EUV radiation are only in a development status. EUV radiation is obtained from the generation of plasmas. Such plasmas can be generated by the strong electrical discharge of gases and are called gas discharge produced plasma (GDPP), or can be generated by laser produced plasma (LPP), i.e. by focussing of laser radiation to a small volume. Due to high optical losses of EUV radiation in the beam forming mirror optics of EUV photolithographic systems, the EUV beam source has to provide a rather large EUV beam power at the exposure wavelength of 13.5 nm with a bandwidth of 2%.

Further, the beam forming optical elements for the EUV spectral range (wavelength range: approx. 1 nm-100 nm, photon energies: approx. 12 eV-1240 eV) are complex, have a high optical loss and are expensive.

As a result the usage of a well-known scanning electron microscope for the analysis of EUV photolithographic masks significantly facilitates and accelerates the development of these masks as well as will considerably lower their manufacturing costs.

In a further aspect, the at least one electron source may be operable to generate electron beams with multiple energies.

In still another aspect the scanning electron microscope further comprises at least one means for providing at least one precursor gas at a position the electron beam hits the photolithographic mask. By this modification the scanning electron microscope can be used to repair defects of both, the absorber layer defects and the multi-layer structure of photolithographic masks.

4. DESCRIPTION OF THE DRAWINGS

In the following detailed description presently preferred embodiments of the invention are described with reference to the drawings, wherein:

FIG. 1 schematically shows a cross-section of an interaction volume generated by an incident electron beam in a sample;

FIG. 2 depicts a two-dimensional schematic collision or scattering cascade of a single electron within the sample;

FIG. 3 schematically indicates the energy gap of the most inner electron shells without fine structure;

FIG. 4 schematically represents interaction volumes generated by an electron beam with a low energy (a) for a sample with a low atomic number Z and (b) for a sample with a high atomic number Z;

FIG. 5 schematically represents interaction volumes generated by an electron beam with a high energy (a) for a sample with a low atomic number Z and (b) for a sample with a high atomic number Z;

Figure 11:
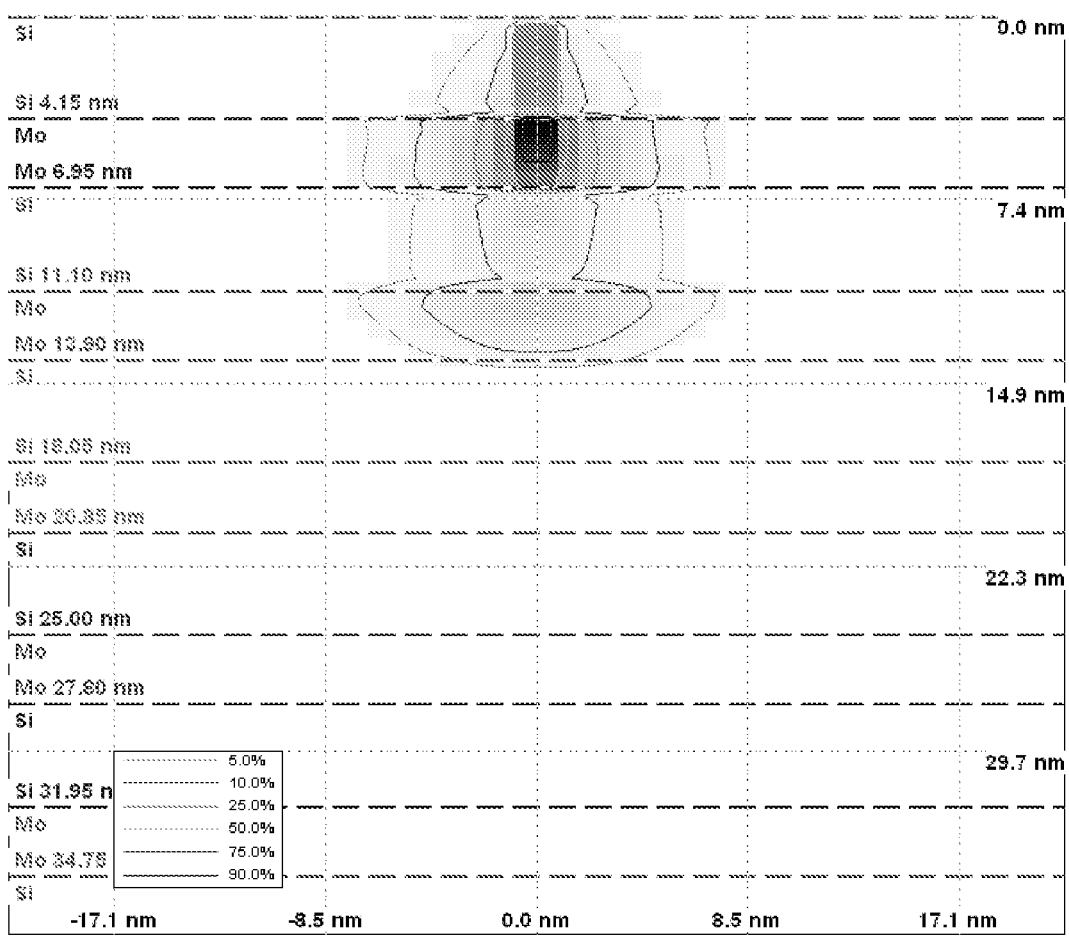
FIG. 11 shows a simulation of the generation area of backscattered electrons in a Si Mo multi-layer system produced by an electron beam of 1 key.
Figure 12:
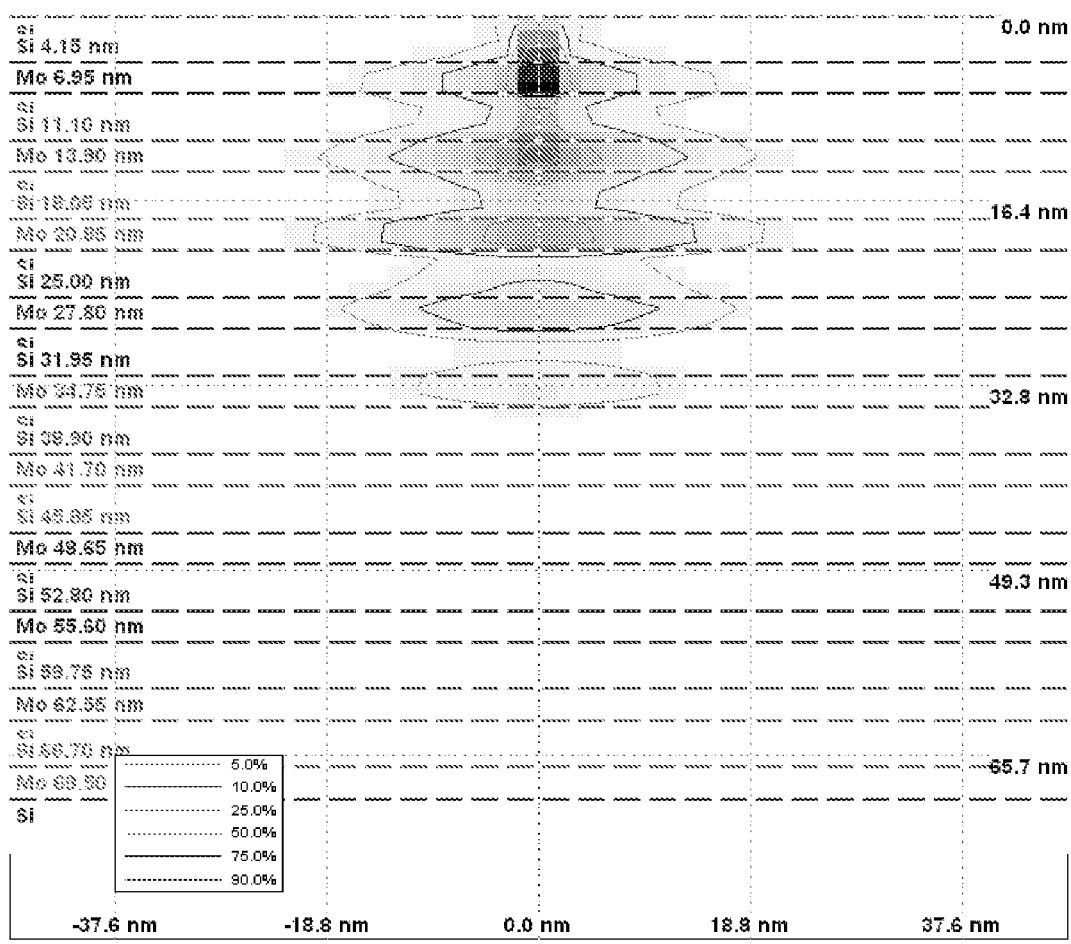
Figure 14:
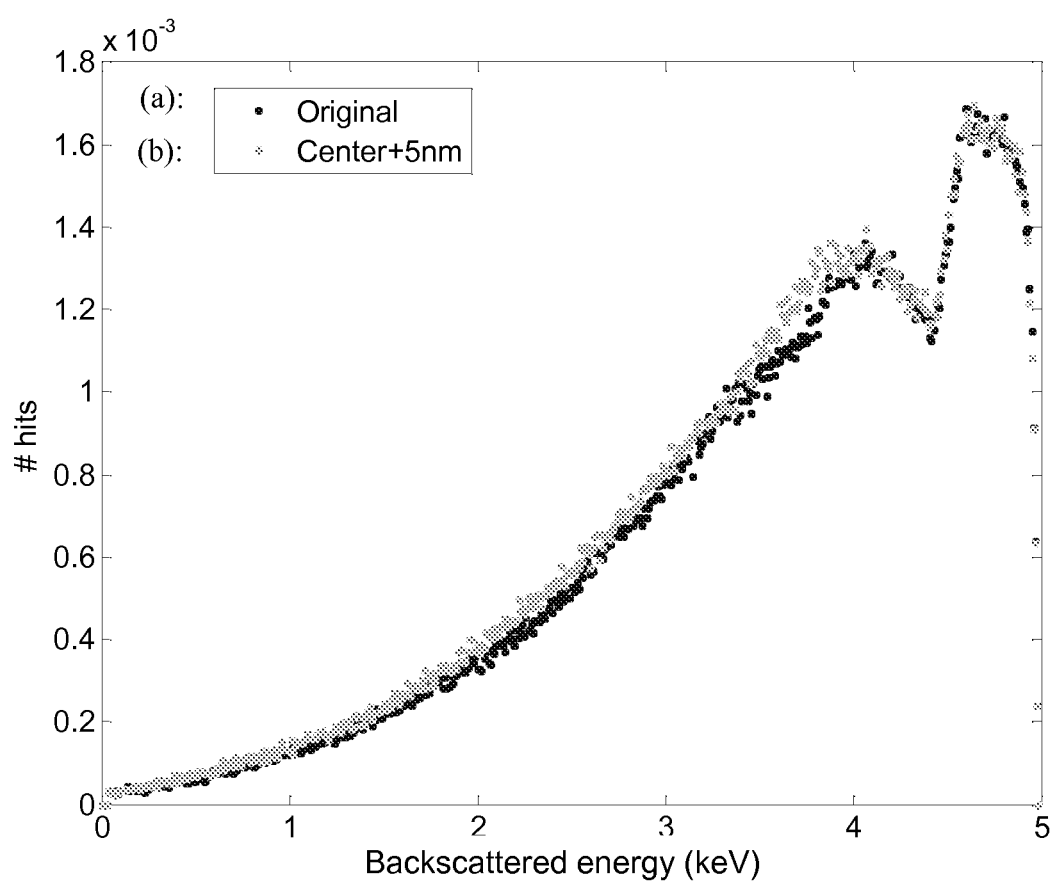
Figure 15:
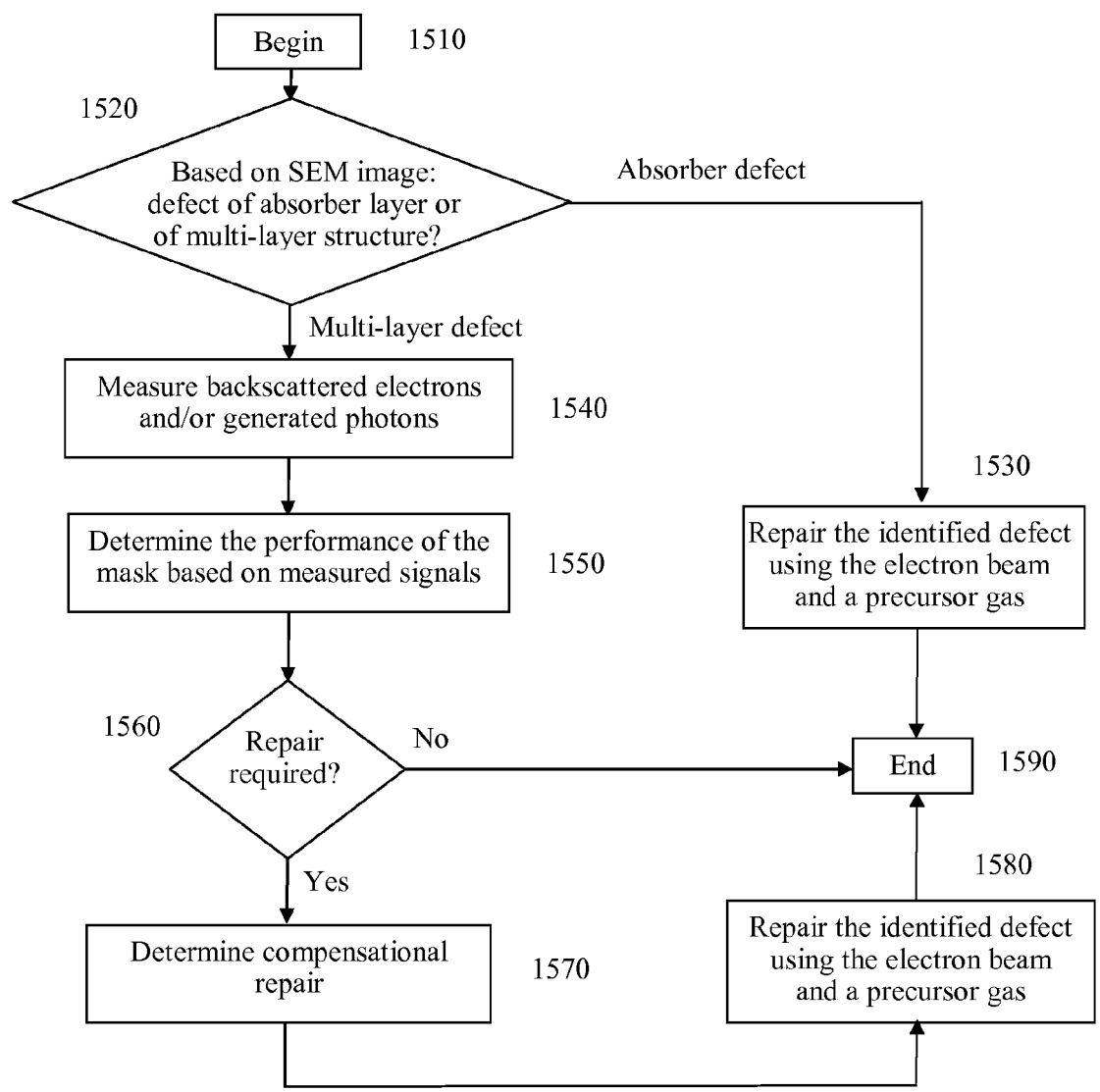

FIG. 12 repeats the simulation of FIG. 11 with an electron beam energy of 2 key;

FIG. 13 (a) represents simulation results of the generation area of backscattered electrons in a system of five Si Mo layers with a layer thickness of 10 nm produced by an electron beam of 5 keV, (b) represents simulation results FIG. 13(a) wherein the second Mo layer has a thickness of 15 nm instead of 10 nm;

FIG. 14 indicates the energy resolved distribution of backscattered electrons of the simulations of FIG. 13(a) and FIG. 13(b);

FIG. 15 shows a flowchart illustrating an embodiment of a mask repair method.

5. DETAILED DESCRIPTION OF PREFERRED EMBODIMENTS

In the following, preferred embodiments of the inventive method and of the inventive apparatus are described in detail.

Figure 1:
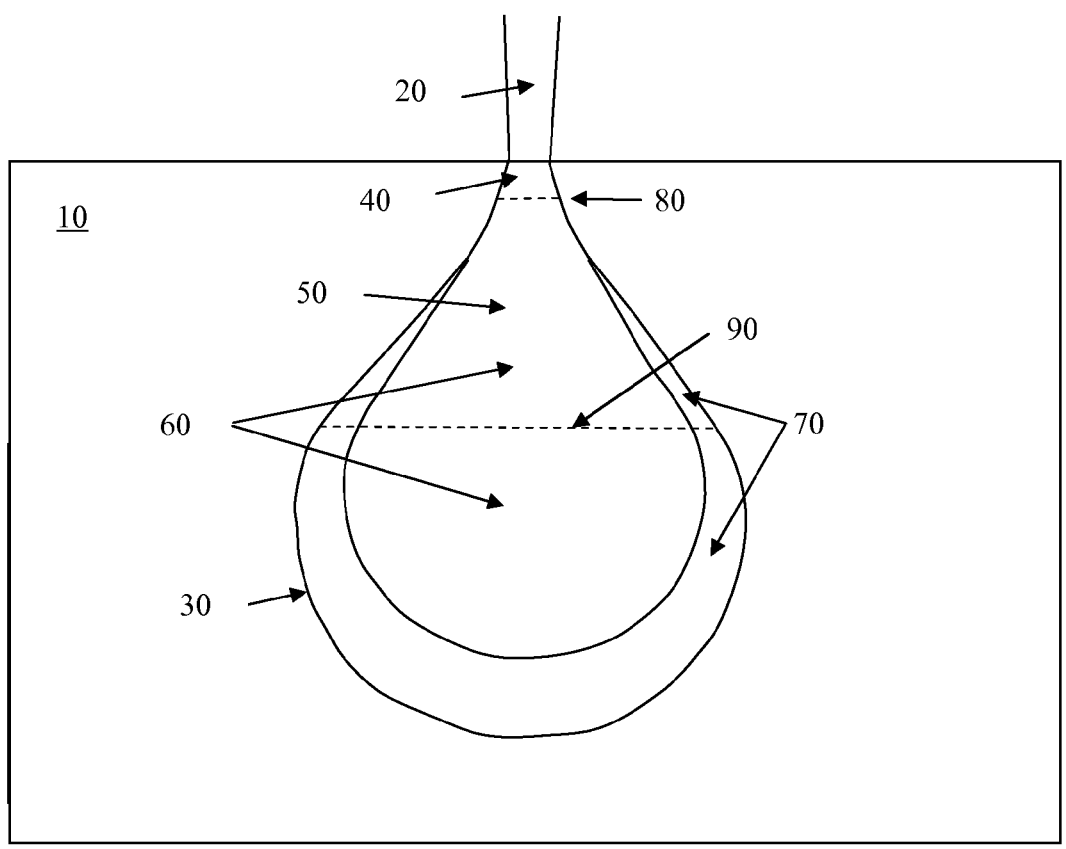

FIG. 1 shows a cross-section of an interaction volume 30 of an electron beam 20 incident on a sample 10. When the electron beam 20 having a kinetic energy in the range of about hundred electron volt (eV) to a few tens of kilo electron volt (keV) strikes the sample 10, the electrons of the electron beam 20 interact the electrons and atomic nuclei of the sample 10. The electrons of the beam 20 will scatter through the sample 10 within a defined area called interaction volume 30.

Figure 2:
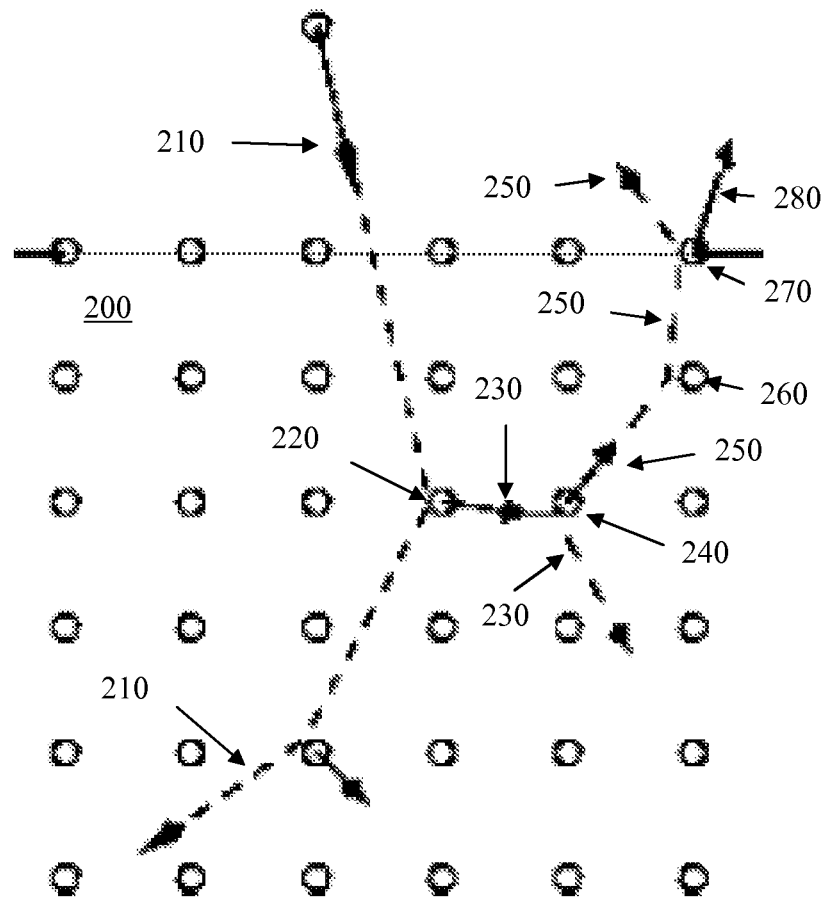

An exemplary path of a single electron 210 in a sample 200 is illustrated in FIG. 2. After entering the sample 200, the electron 210 is scattered in the electromagnetic field of an atomic nucleus 220 of the sample 200. During the interaction process the electron 210 transfers energy to an electron 230 in an inner electron shell of the atomic nucleus 220. The energy transferred by the electron 210 to the electron 230 brakes the electron 210 and releases or knocks the electron 230 from its inner shell in nucleus 220. The released electron 230 is scattered in the strong electromagnetic field of atomic nucleus 240 and releases an electron 250 from an inner shell of nucleus 240. After having performed further scattering events in the electromagnetic fields of atomic nuclei 260 and 270, the electron 250 leaves the sample 200 close to the nucleus 270. Apart from releasing electrons, photons of different wavelengths are also generated during scattering events. These photons are not indicated in FIG. 2. Only one photon 280 generated during the scattering event in the electromagnetic field of nucleus 270 is depicted in FIG. 2.

Now back to FIG. 1, during the interaction of the electrons of the electron beam 20 in the interaction volume 30, secondary products like secondary electrons, backscattered electrons, photons, heat and an electrical current are formed. Secondary electrons have a low energy ($\leq 50$ eV). They are generated within the overall interaction volume 30. However, due to their low energy secondary electrons can leave the sample 10 only from a small layer 40 below the sample surface. Dashed line 80 indicates schematically the depth of layer 40.

Electrons of the electron beam 20 also generate backscattered electrons everywhere within the interaction volume 30. As illustrated in FIG. 2, backscattered electrons are usually produced by multiple scattering events. Therefore, they travel considerable distances within sample 10 during the backscattering process. Dashed line 90 separates the region from which backscattered electrons can leave sample 10, which is the upper part 50 of the interaction volume 30, from the area where the backscattered electrons can not escape from the sample 10 due to multiple scattering events. This is the portion of the interaction volume 30 below the dashed line 90. Thus, although the interaction volume 30 may have a significant extent in the direction of the electron beam 20, backscattered electrons leaving the sample originates only from the portion 50 of the interaction volume 30. Thus, the spatial resolution of the backscattered electrons is higher than indicated by the interaction volume 30.

As already mentioned, photons are also created during the interaction of the beam electrons 20 with the electrons and atomic nucleus of the sample 10. Photons are again generated within the overall interaction volume 30. Similar to the energy interval of the incident electron beam 20, the spectral range of the generated photons may comprise several orders of magnitude. It is divided into two regions:

(a) The first one is called continuum x-rays as the minimum wavelength is in the range of x-ray photons. Continuum x-rays are created in every portion 70 of the interaction volume 30. They are produced when striking beam electrons 20 are slowed to varying degrees by the strong electromagnetic field of atomic nuclei in the sample 10. All degrees of electron braking are possible and, thus, the resulting photons have a continuous range of all energies. The highest photon energy that can be produced by electrostatic braking has an energy equivalent to the kinetic energy of the beam electrons 20. Continuous x-ray photons may escape the sample 10 from all portions 70 of the interaction volume 30.

Figure 3:
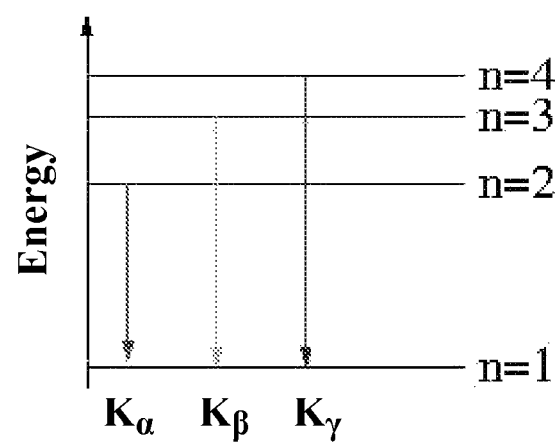

(b) The beam electrons 20 may knock a small fraction of electrons out of inner shell orbitals, in a process call inner-shell ionization. An atom remains only ionized for an extremely short period (~$10^{-14}$ s) before inner-shell vacancies are filled by outer-shell electrons, emitting so-called characteristic x-ray photons. FIG. 3 represents a simplified energy spectrum of characteristic x-ray photons.

As the energy gap between different inner shells or inner shell orbitals is specific or characteristic for each element, characteristic x-ray photons can be used to identify different elements within sample 10. Thus, the composition of the sample 10 can be determined from the spectrum and intensity distribution of the characteristic x-ray radiation. As a consequence of their higher energy characteristic x-ray photons can escape from the portions 60 of the interaction volume 30. This volume is larger than the portion 50 of the backscattered electrons, but smaller than the portion 60 of the continuous x-ray radiation.

Figure 4:
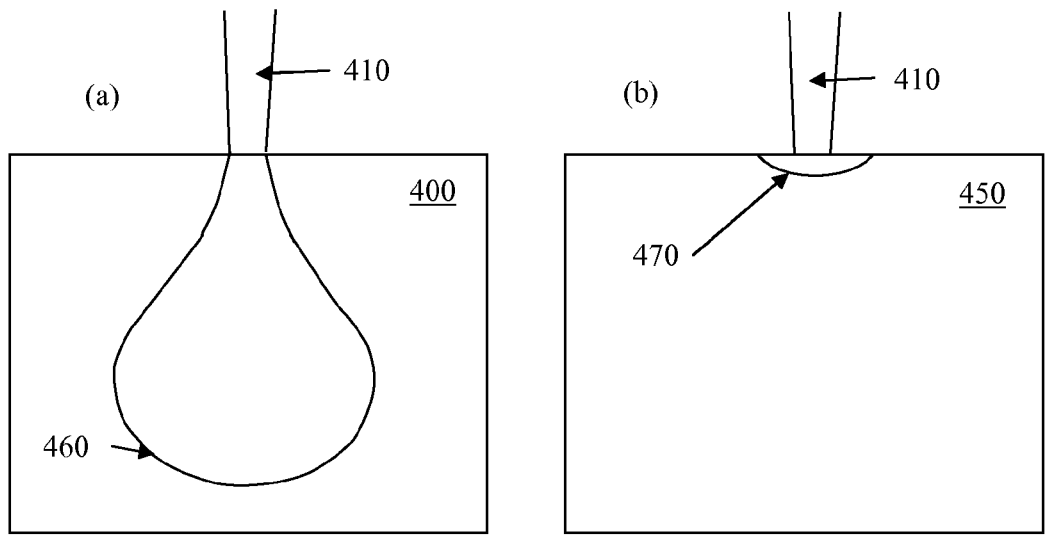

FIG. 4 schematically depicts that the volume of the interaction volume depends on the atomic number Z of the element forming the sample. The atomic number Z indicates the number of protons in the atomic nucleus of the respective element and is thus proportional to the strength of the electromagnetic field close to the atomic nucleus. FIG. 4a shows the interaction volume 460 for a sample 400 with a low Z, such as a silicon layer (Z=14) created with an electron beam 410 of low energy (e.g. 500 eV). Despite the low electron beam energy 410, the interaction volume 460 has a considerable depth. On the other hand, FIG. 4b represents the interaction volume 470 of a sample 450 consisting of elements with a high Z, as for example molybdenum (Z=42). In this case, the low electron beam energy 410 in combination with the strong electromagnetic field of the molybdenum atomic layer results in an extremely small interaction volume 470.

Figure 5:
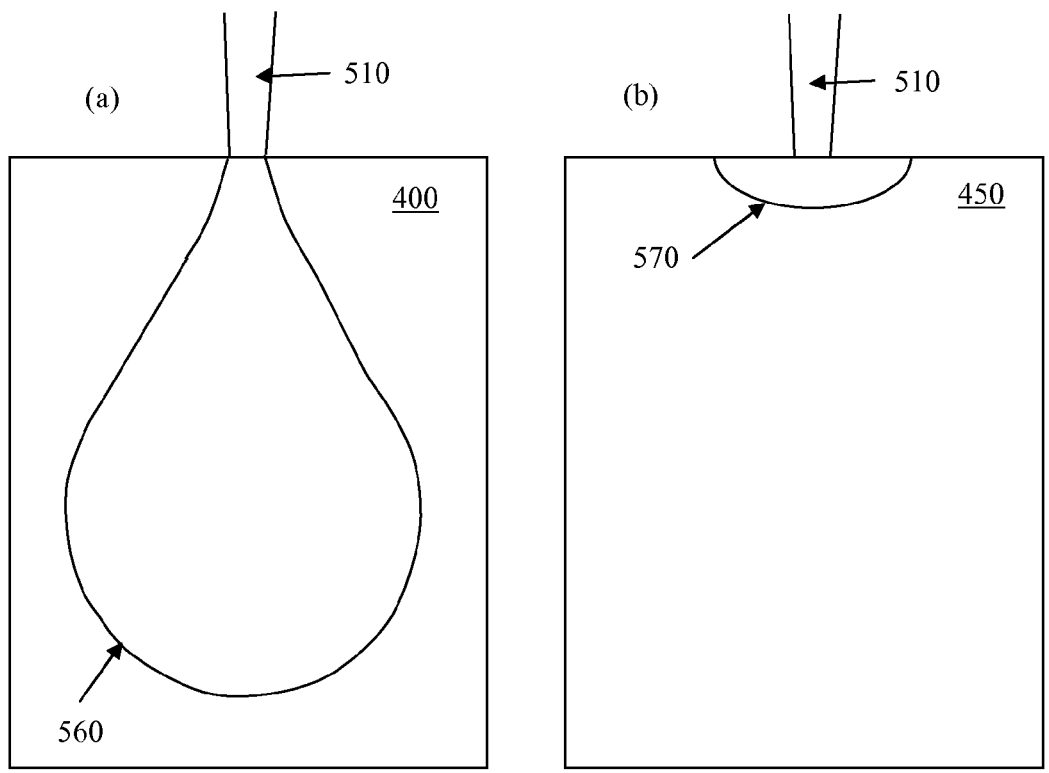

FIG. 5 repeats the condition of FIG. 4 with the usage of an electron beam 510 with a high kinetic energy, as for example 15 keV. By the high energy electron beam 510 the interaction volume 560 for the low Z sample is significantly increased compared to the low energy interaction volume 460 of FIG. 4. FIG. 5b indicates that the high energy electron beam 510 also increases the interaction volume 570 of the high Z sample 450. The increase in the depth of the interaction volume 570 leads to an increase in the radius from which backscattered electrons and reflected photons can be detected. FIGS. 4 and 5 demonstrate that the beam energy can be used as a parameter to investigate the depth profile of a sample.

The yield η of backscattered electrons in a film as a function of the thickness d is given by $$\eta(d) = \frac{\pi e^4 Z^2 N_A}{4(4\pi\varepsilon_0)^2 A E^2} \cdot \rho \cdot d \quad (1)$$

where e is the elementary charge, Z is the atomic number, $N_A$ is Avogadro's constant, $\in_0$ denotes the dielectric constant, A is the atomic weight, E is the energy of the incident electron beam and ρ denotes the density of the sample film. This equation is taken from the textbook "Scanning of electron microscopy" of L. Reimer, p. 138, $2^{nd}$ Edition, October 1998, Springer Verlag. It indicates that the yield η of the backscattered electrons is a function of Z as well as of the sample film density ρ. Thus, by just measuring the yield η(d) of backscattered electrons as a function of the film thickness d, the variation of the thickness d can not be distinguished from a variation in the composition resulting in a change in Z and/or ρ.

Figure 6:
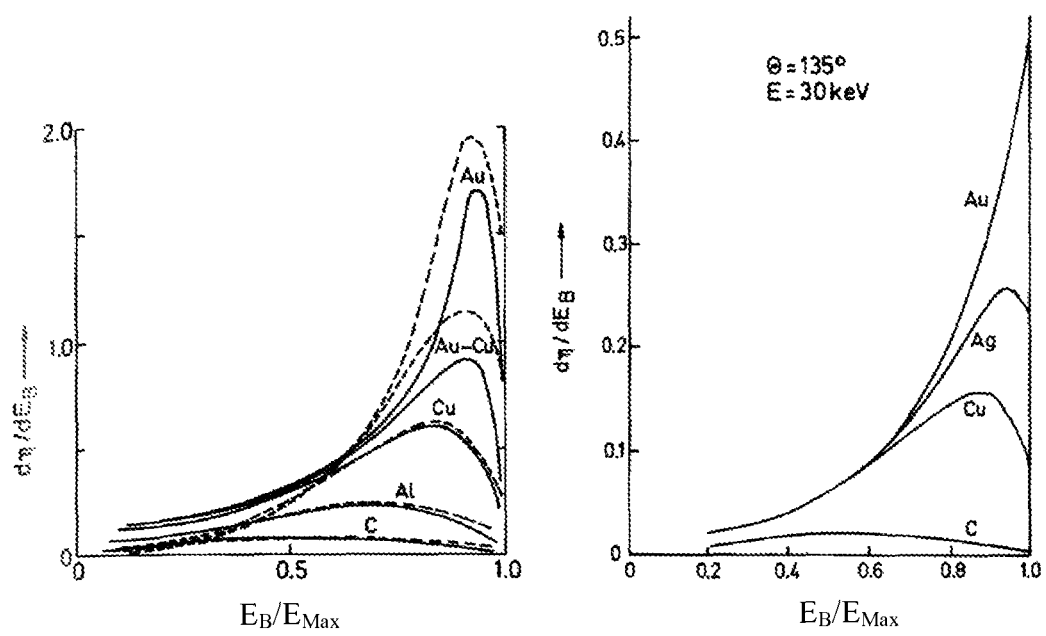
FIG. 6 depicts measured energy spectra of backscattered electrons as a function of the energy of backscattered electrons for samples of various elements (left) and measured energy spectra under an exit angle of 135° (right)

However, as is depicted in FIG. 6, apart from the yield, the energy distribution or the energy spectra $d\eta/dE_B$ of backscattered electrons can also be measured. The diagrams of FIG. 6 are also taken from "Scanning of electron microscopy" of L. Reimer, p. 149, $2^{nd}$ Edition, October 1998, Springer Verlag. The energy $E_B$ of backscattered electrons is normalized to the maximum possible energy $E_{Max}$ which is essentially identical to the energy E of the incident electron beam. The beam energy E is 30 keV and the exit angle of the backscattered electrons amounts 135° measured from the sample surface. As can be seen from FIG. 6 the energy spectrum of the backscattered electrons follows a curve which is specific for the element forming the sample. It is recognized from FIG. 6 that the energy distribution is rather flat for low Z elements, but has a peak for elements with a larger proton number. This peak becomes higher for heavier elements having an increasing number of protons. Additionally, the peak shifts with increasing Z towards $E_{Max}$. FIGS. 4 to 6 and equation 1 demonstrate that the strong electromagnetic field of high Z elements elastically or nearly elastically scatters a larger portion of the incident electrons back towards the sample surface. This means that measurements of the backscattered electrons contain information which allows determining the composition of the sample.

Consequently, both the electrons and the photons generated by an incident electron beam can be used to analyse or determine the composition of a sample.

Figure 7:
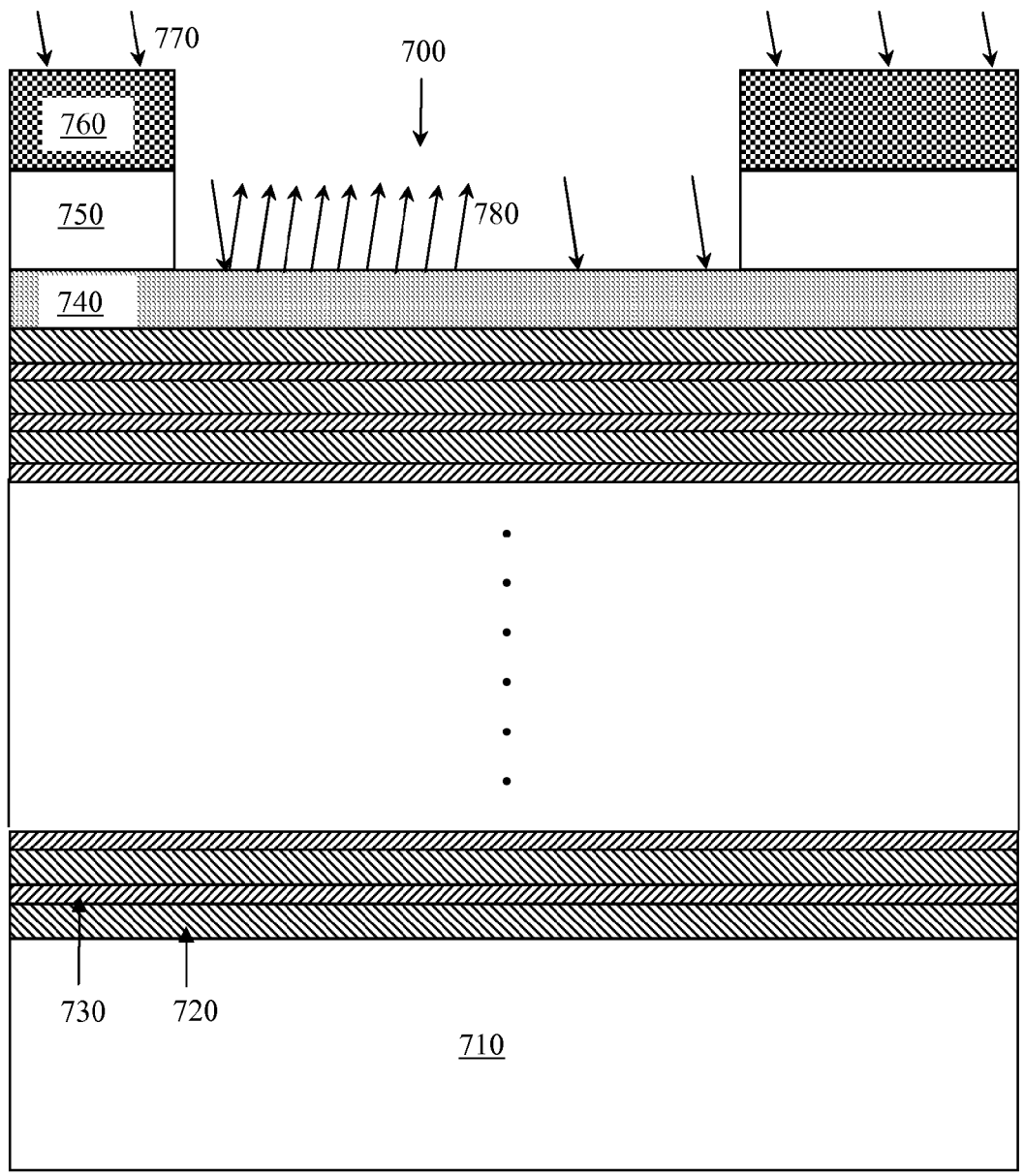
FIG. 7 shows in cross-section a schematic view of an EUV photolithographic mask.

In the following an electron beam will be applied to determine the composition of a photolithographic mask for the EUV wavelength region. FIG. 7 shows a schematic cross-sectional view of a photolithographic mask 700 for an exposure wavelength of 13.5 nm. Different from presently applied photolithographic masks, the mask 700 is a reflective optical element based on a multi-layer mirror structure. The multi-layer system of photolithographic mask 700 is deposited on a suitable substrate 710, such as a silicon wafer or a glass substrate. The multi-layer system comprises of 40 pairs of alternating molybdenum (Mo) 720 and silicon (Si) layers 730. The thickness of each Mo layer 720 is 4.15 nm and that of the Si layer 730 amounts to 2.80 nm. In order to protect the multi-layer structure, a capping layer 740 of silicon with a native oxide of 7 nm depth is arranged on top of the structure. In the multi-layer system, the Mo layers 720 layers represent regions of high refractive index for the EUV radiation and the Si layers 730 represent regions of low refractive index, respectively. Together they form a dielectric mirror for the EUV radiation.

The multi-layer structure on the substrate 710 acts a mirror for EUV electromagnetic radiation. In order to become a photolithographic mask 700, a buffer layer 760 and an absorber layer 770 are additionally deposited on the capping layer 750. For some EUV mask types a buffer layer 750 is discussed. This layer is located between the absorber 760 and the capping layer 740. The buffer layer 750 helps to etch the material of the absorber layer 760 without damaging the capping layer 740. Thus, the buffer layer 750 makes the plasma etch process more simple. The disadvantage of a buffer layer 750 is a more complex mask stack increasing the stack height. For photolithographic mask features with a high aspect ratio the probability of a pattern collapse increases with the stack height. The absorber layer 760 comprises a material having a large absorption constant for photons in the EUV wavelength range, as for example Tantalum nitride. A thickness of about 70 nm is sufficient to absorb essentially all EUV photons 770 incident on the absorber layer 760. In contrast, the majority of the photons 770 incident on the capping layer 740 is reflected as photons 780. In this context as well as on further positions of this description the term "essentially" means a numeric value of a quantity within its measurement limit.

Figure 8:
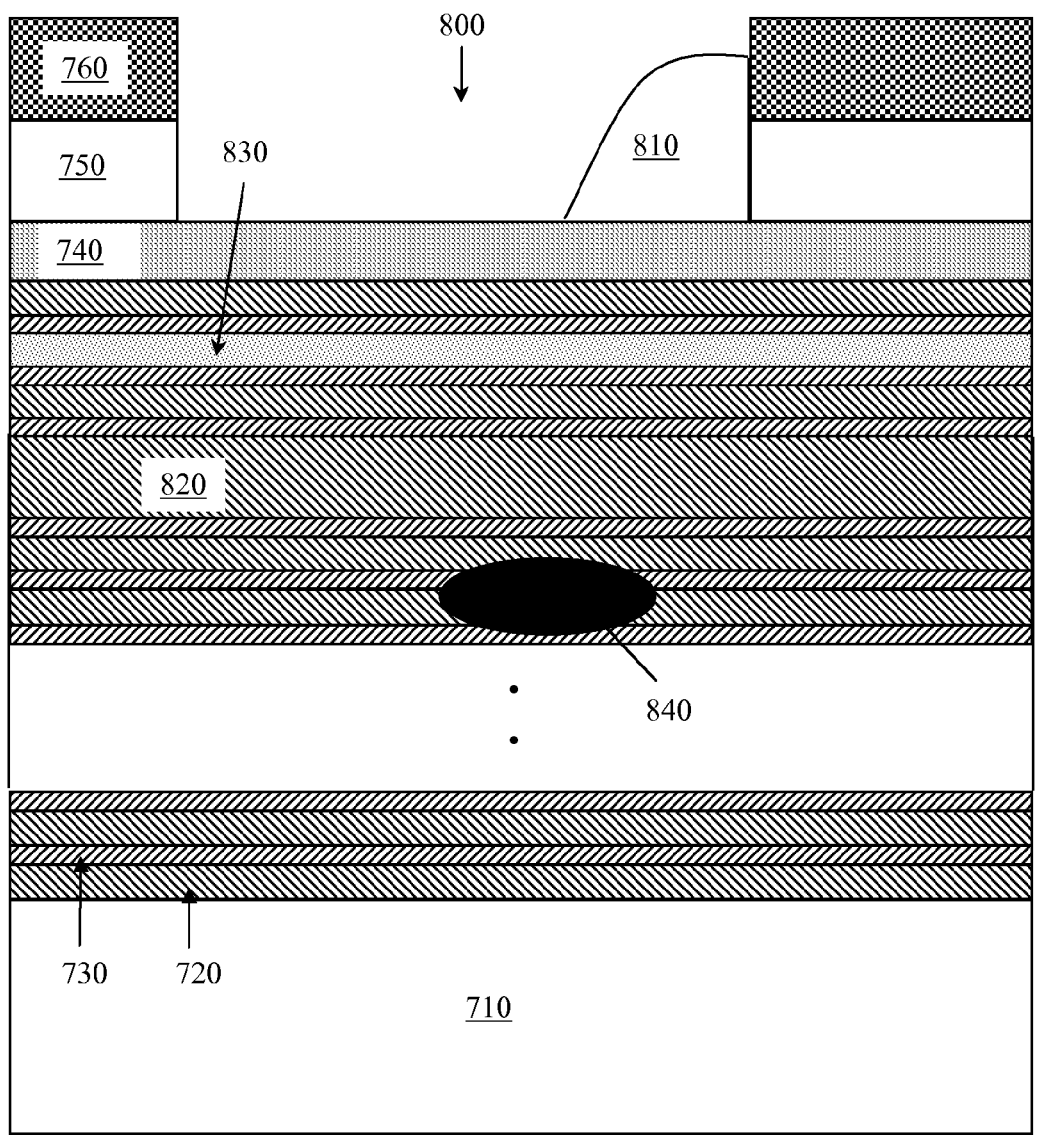
FIG. 8 shows a schematic representation of an EUV photolithographic mask having different defects.

In FIG. 8 several possible defect of the photolithographic mask 700 of FIG. 7 are indicated in mask 800. On top of the capping layer 740 there is excessive material 810 on the multi-layer structure which may absorb EUV photons and/or disturb the phase of the incident and/or reflected EUV radiation. In the multi-layer system, defects may occur when the Mo and/or the Si layer thickness deviates from the predetermined thickness. A Mo layer 820 with a too large thickness is indicated in FIG. 8. A further defect may result from a layer which has not the predetermined composition. In FIG. 8, this kind of defect is represented by a contaminated Mo layer 830. Further, as the thicknesses of the Mo and Si layers are only a few nm, even a small portion of different material embedded in the multi-layer system may disturb the path of the EUV photons and thus acting as a defect of the photolithographic mask. In FIG. 8 the existence of such a defect is represented and denoted with 840. FIG. 8 represents only some defects out of the variety of defects which may occur on a EUV mask 700. In particular, FIG. 8 does not indicate a defect of the absorber layer 760.

Figure 9:
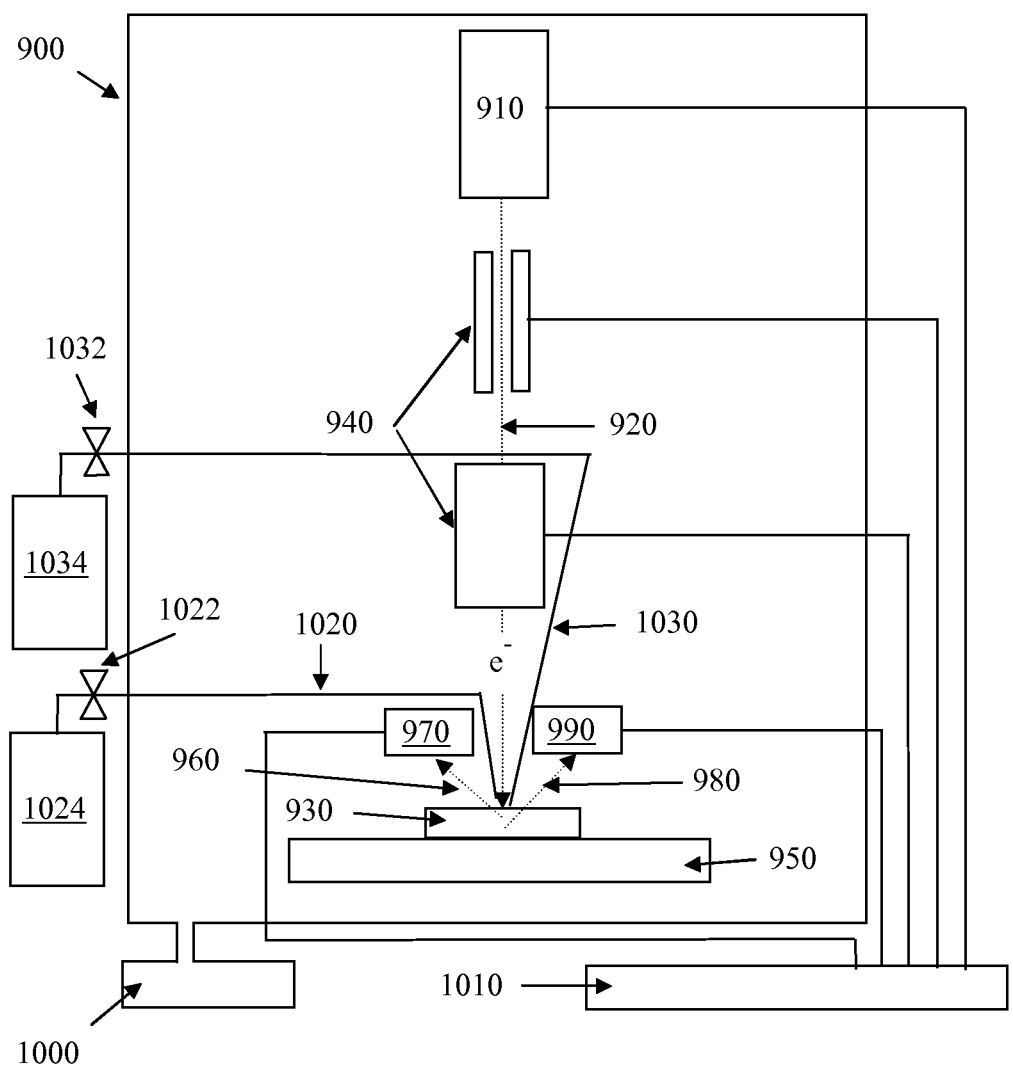
FIG. 9 represents a schematic diagram of an apparatus with an electron source, beam adjusting means, detectors for electrons and photons, a computing means and means for providing a precursor gas.

FIG. 9 shows a scanning electron microscope 900 with which the defects of photolithographic mask 800 represented in FIG. 8 can be analyzed. An electron source or electron gun 910 produces an electron beam 920 with an adjustable kinetic energy. The beam energy can vary from about 100 eV to about 100 keV depending from the sample 940 to be investigated and the required resolution within the sample 940. The beam current can be adjusted from about 0.5 pA to about 50 nA The beam forming elements for forming and adjusting the spot diameter of the electron beam on the sample surface 930 are omitted in FIG. 9. The minimum spot diameter on the sample surface 930 is approximately 2 nm This dimension limits the spatial resolution in the plane perpendicular to the electron beam 920. Deflection elements 940 enable scanning of the electron beam 920 across the sample 930. The sample 930 is mounted on a sample holder 950. Sample holder 950 may be adjustable in two or three directions.

The electron beam 920 repeatedly scans the sample 930 with various beam energies. Backscattered electrons 960 are measured with the detector 970. Detector 970 may be of scintillator or semiconductor type. Detector 970 may be further rotatable in polar direction to collect backscattered electrons 960 leaving the sample 930 with different exit angles. Thus, an angular distribution of the backscattered electrons 960 can be analysed. Alternatively and/or additionally a magnetic field may be used to focus the backscattered electrons 960 onto the detector 970. Furthermore, the detector 970 may be mounted in a "doughnut" type arrangement concentric with the incident electron beam 920 (not shown in FIG. 9). Moreover, a retarding electric field may be applied to prevent electrons below a certain energy to reach the detector 970.

FIG. 9 also shows a detector 990 to measure photons 980 leaving the surface of the sample 930. The detector 990 can again be of scintillator or semiconductor type. Both semiconductor detector variants, the Si(Li) detector and the silicon drift detectors (SDDs) may be applied and allow to directly determine the x-ray photon energy spectrum. This method is called energy dispersive x-ray spectroscopy (EDX). Both detectors 970, 990 may be cooled (not shown in FIG. 9) to enhance their energy resolution. Similar to the detector 970 for the backscattered electrons 960, the detector 990 for generated photons 980 may be movable or mounted in different arrangements in the scanning electron microscope 900.

In the scanning electron microscope 900 of FIG. 9, both the detector 970 for backscattered electrons 960 and the detector 990 for generated photons are installed. As already mentioned above, the analysis of signals measured with both detectors 970, 990 may facilitate the determination of the composition of complex samples 930. However, as previously discussed, the measured signals of each one of the detectors 970, 990 carry all information necessary to determine the composition of sample 930, so that detector 970 and detector 990 may also be used alone.

The signals measured with detector 970 and detector 990 are transmitted to computing means 1010. Computing means 1010 may be a microprocessor, a general purpose processor, a special purpose processor, a CPU (central processing unit), a GPU (graphic processing unit) or the like. It may be arranged in the control unit of the scanning electron microscope 900, or may be a separate unit such a PC (personal computer), workstation, etc. The computing means 1010 may further comprise I/O (input/output) units like a keyboard, touchpad, mouse, a video/graphic display, a printer, etc. In addition, the computing means 1010 may also comprise a volatile and/or a non-volatile memory. The computing means 1010 may be realized in hardware, software, firmware or any combination thereof. Moreover, the computing means 1010 may control the electron source 910, the adjusting means 940 and the settings of the detectors 970 and/or 990. Although not shown in FIG. 9, the computing means 1010 may also control the high vacuum within the scanning electron microscope 900 via a pressure sensor (not indicated in FIG. 9) and the vacuum pump 1000.

The computing means 1010 analyzes the signals of the detector 970 and/or of the detector 990 and determines the composition of the sample 930. In case, the sample 930 is the photolithographic mask 700, the computing means 1010 determines the thickness of the capping layer 740 and the portions of silicon and oxygen. Further, the computing means 1010 extracts from the measured signals of the detectors 970 and/or of the detector 990 the thickness of the alternating layers as well as their content of molybdenum and silicon. Moreover, the computing means 1010 determines the position, the thicknesses as well as the composition of the buffer layer 750 and the absorber layer 760.

When the sample 930 comprises the mask 800 having several defects 810, 820, 830 and 840, the information contained in the measured signals of the backscattered electrons 960 and/or generated photons 980 allow localising these defects and analyzing their composition. In addition, the portion of the mask 800 containing the defect can be compared with a portion without defect.

The scanning electron microscope 900 may further comprise a nozzle 1020 with which a first precursor gas can be provided at the position of the sample 930 the electron beam 920 hits the sample 930. The flow rate of the first precursor gas through the nozzle 1020 can be controlled by a metering valve 1022. As indicated in FIG. 9, the metering valve 1022 may be arranged outside of the scanning electron microscope 900. In order to precisely control the flow of the first precursor gas the valve 1022 may also be arranged close to the opening of the nozzle 1020 (not shown in FIG. 9). The first precursor gas is stored in a tank 1024. The tank may be temperature controlled. Moreover, a temperature controlling unit can be arranged around the nozzle 1020 to provide the first the precursor gas at a predetermined temperature (not indicated in FIG. 9). The first precursor gas may be an etching gas which removes in combination with the electron beam 920 excessive materials of the absorber layer 760 of the photolithographic mask 800.

Additionally, the scanning electron microscope 900 may also comprise a nozzle 1030 through with a second precursor gas can be provided at the position of the sample 930 the electron beam 920 hits the sample 930. The two precursor gases can be provided alternating and/or simultaneously. The metering valve 1032 controls the flow of the second precursor gas from the storage tank 1034 through the nozzle 1030. As described in the previous paragraph, the metering valve 1032 may be arranged at any position between the storage tank 1034 and the opening of the nozzle 1030. The storage tank 1034 may include a unit to control the temperature of the second precursor gas. Furthermore, a temperature controlling unit may be arranged between the storage tank 1034 and the metering valve 1032 and/or close to the opening of the nozzle in order to provide the second processing gas at a predetermined temperature at the position the electron beam 920 hits the sample 930. The electron beam 920 decomposes the second precursor gas at the position the absorber layer 760 of the photolithographic mask miss absorber material. The corresponding component of the second precursor gas deposits on the absorber layer 760 to remove the defect. To efficiently remove the volatile components of the first and/or second precursor gases a suction nozzle with a pump may additionally be arranged close to the nozzles 1020, 1030 (not shown in FIG. 9).

Figure 10:
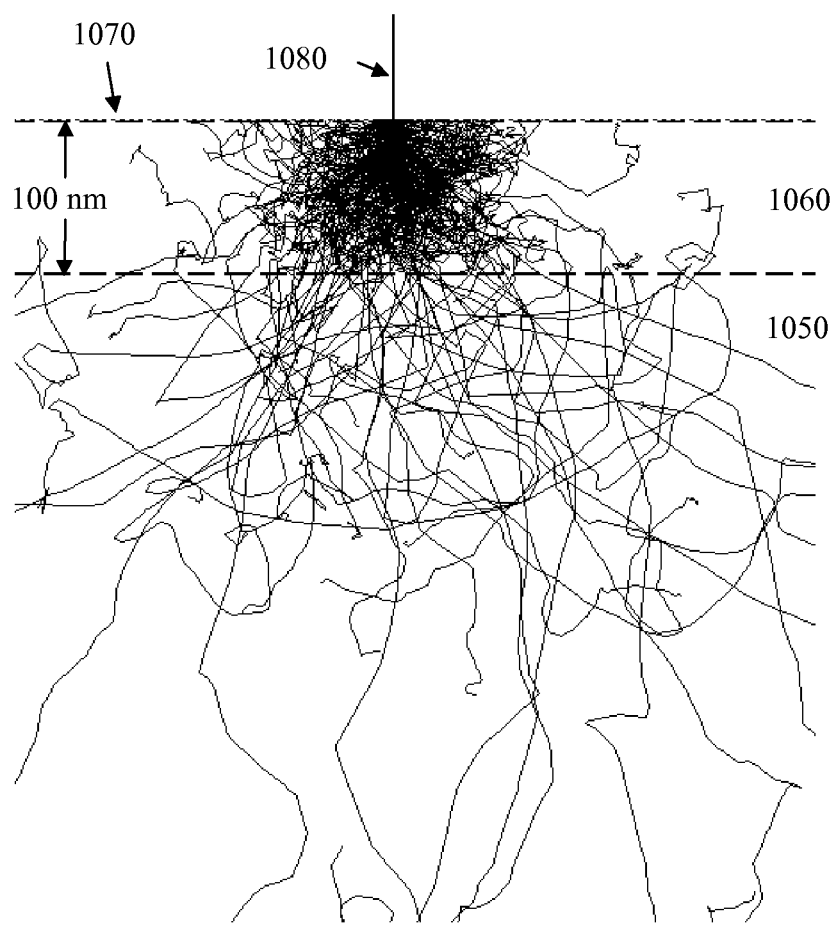
FIG. 10 shows a simulation of the interactions of electrons of an electron beam in a gold stack with a depth of 100 nm.

The process to determine the structure and composition of photolithographic masks 700, 800 may be supported by simulating the effect of the incident electron beam 920 on the sample 930. FIG. 10 represents the collision or scattering cascades of an electron beam 1080 incident on a gold layer 1060 with a layer thickness of 100 nm arranged on a silicon substrate 1050. The incident electron beam 1080 has a kinetic energy of 10 keV. FIG. 10 represents the accumulation of the scattering cascades of many individual electrons. A scattering cascade of an individual electron is schematically represented in FIG. 2.

FIG. 11 depicts a simulation of the interaction of an electron beam with a silicon (Si) molybdenum (Mo) multi-layer system. The electrons strike the multi-layer system from above with an energy of 1 keV. The grey-shaded areas denote the areas where backscattered electrons are generated. Due to the high difference in the atomic number of Si (Z=14) and Mo (Z=42) backscattered electrons are nearly exclusively generated in the Mo layers. At the energy of 1 keV more than 50% of the backscattered electrons are generated in the first Mo layer.

FIG. 12 shows the simulation of the multi-layer system of FIG. 11 but now with an electron beam having an energy of 2 keV. As indicated in FIGS. 4 and 5, the higher energy beam penetrates deeper into the Si Mo multi-layer system. Similar to FIG. 11, the vast majority of backscattered electrons are again generated in the Mo layers. However, different to FIG. 11, a portion of 50% of backscattered electrons is now generated in the first two Mo layers.

FIG. 13(*a*) represents a simulation of backscattered electrons of a five Si Mo layer system, each layer having a thickness of 10 nm. The incident electron beam has an energy of 5 keV. In FIG. 13(*b*), the second Mo layer has a thickness of 15 nm instead of 10 nm as in FIG. 13(*a*). As can be seen by the comparison of FIGS. 13(*a*) and 13(*b*), the thickness deviation of the second Mo layer modifies the spatial distribution of the backscattered electron generation volume.

This modification of the spatial distribution of the generation volume of the backscattered electron is also manifest in the energy spectra of the backscattered electrons leaving the five Si Mo layer system of FIG. 13(*a*) and FIG. 13(*b*). This is shown in the simulated energy resolved spectrum of the backscattered electrons of FIG. 14. This means that already a small thickness deviation of a layer in the multi-layer system can be detected in the signals of backscattered electrons.

FIGS. 10-14 demonstrate that simulation is a valuable tool for analyzing the structure and composition of EUV photolithographic masks. In particular simulation can be applied in combination with measured signals of backscattered electrons and/or generated photons to resolve defects in EUV masks.

When the composition of the EUV mask is determined, the computing means 1010 can again be applied to determine the performance of the mask when EUV photons are incident on it. The interaction of the EUV photons is essentially dominated by the two effects: absorption and scattering or reflection. The basic physical laws of both effects are well-known and understood. Therefore, similar to the above discussed simulation of an incident electron beam, the interaction of an EUV photon beam on the EUV mask can be simulated. Thus, the performance of an EUV mask can be determined if its composition is known.

The description concentrates on an electron beam scanning and thus probing the EUV mask, or more generally a sample. However, the inventive method is not limited to the usage of electrons for scanning the sample. Apart from electrons, a photon beam of a known wavelength which is tuneable across a certain spectral range can also be applied to scan the EUV mask. Moreover, an ion beam having an energy to essentially not damage the sample can also be utilized for scanning the sample and thus producing backscattered electrons and/or generated photons which are then used to analyze the sample.

When the analysis of the EUV mask in the scanning electron microscope 900 reveals that the mask has a defect 810, 820, 830, 840 or any other, the scanning electron microscope 900 or a modified apparatus having a tuneable electron beam 920 can be used to repair the identified defect. The flowchart 1500 of FIG. 15 illustrates this method. The method begins at step 1510 when the sample or the EUV mask is inserted in the scanning electron microscope 900. At step 1520, a SEM (scanning electron microscope) image is used to decide, whether the defect can be identified as a defect of the absorber layer 760. If this is true, no more analysis needs to be done and the defect is repaired in block 1530. The repair is performed by scanning the defect area with the electron beam 920 of the scanning electron microscope 900 while providing a respective precursor gas through the nozzle 1020, 1030 at the position of the defect. The electrons of the electron beam 920 trigger a chemical reaction of the gas molecules of the precursor gas with the surface of the absorber defect. Depending on the kind of defect, a first precursor gas or combinations of first precursor gases or a second precursor gas or combinations of second processor gases are used to remove excessive absorber material or to deposit missing absorber material at the defect location of the absorber layer 760 of the photolithographic mask 800.

If it is detected at decision block 1520 that the defect is not a defect of the absorber layer 760, the surface of the photolithographic mask 800 is scanned with electrons 920 and the backscattered electrons and/or the generated photons are measured and analysed at block 1540. At block 1550, the performance of the photolithographic mask 800 is determined from this set of data. This can for example be performed by the computing means 1010 of the scanning electron microscope 900. It is then decided at decision block 1560 whether the discrepancy between the determined and the predetermined performance of the photolithographic mask 800 requires the repair of the identified defect of the multi-layer structure. When a repair of the defect is not necessary, no more action is required for the identified defect of the multi-layer or Mo Si structure, and the method ends at block 1590. When the defect of the multi-layer structure needs to be repaired, a compensational repair is computed at block 1570. For example, this computation can again be performed by the computing means 1010 of the scanning electron microscope 900. The computational repair modifies the absorber layer 760 of the photolithographic mask 800 in a way to compensate for a defect in the multi-layer structure. Finally, the compensational repair is executed in block 1580 by again using the electron beam 920 of the scanning electron microscope 900 and by providing a precursor gas through the nozzle 1020, 1030 and the method ends for the identified multi-layer defect at block 1590.

The invention claimed is:

1. A method for predicting a performance of a photolithographic mask at a predetermined exposure wavelength, comprising:
   a. repeatedly scanning at least one electron beam with multiple beam energies across at least one portion of the photolithographic mask, wherein the performance of a photolithographic mask is defined by its capability to transmit a predetermined structure or pattern in a photoresist arranged on a wafer;
   b. measuring signals generated by the at least one electron beam interacting with the at least one portion of the photolithographic mask, wherein if the photolithographic mask includes a defect, the signals include a positional information of the defect;
   c. determining whether the defect is a defect of an absorber layer of the photolithographic mask or a defect of a multi-layer structure of the photolithographic mask, and, if the defect is a defect of the multi-layer structure of the photolithographic mask, predicting the performance of the at least one portion of the photolithographic mask at the predetermined exposure wavelength based on the measured signals; and
   d. determining whether a repair of the defect is required based on a discrepancy between the determined performance and a predetermined performance.

2. The method according to claim 1, wherein the photolithographic mask comprises a reflective photolithographic mask.

3. The method according to claim 1, wherein the photolithographic mask comprises a photolithographic mask for an extreme ultraviolet (EUV) exposure wavelength, in particular for a wavelength around 13.5 nm.

4. The method according to claim 1, wherein measuring signals comprises measuring of electrons, in particular measuring backscattered electrons and wherein measuring backscattered electrons comprises measuring a yield of backscattered electrons and/or measuring an energy distribution of backscattered electrons.

5. The method according to claim 1, wherein measuring signals comprises measuring photons, in particular measuring photons using the energy dispersive x-ray spectroscopy (EDX).

6. The method according to claim 1, wherein measuring signals comprises measuring electrons and measuring photons, in particular measuring backscattered electrons and measuring photons using the energy dispersive x-ray spectroscopy.

7. The method according to claim 1, further comprising simulating signals generated by the electron beam interacting with the portion of the photolithographic mask and determining the performance of the portion of the photolithographic mask at the predetermined exposure wavelength evaluating simulated and measured signals.

8. The method according to claim 1, further comprising determining a defect in the performance at the predetermined exposure wavelength of a portion of the photolithographic mask by evaluating measured signals of a portion of the photolithographic mask and/or by evaluating measured and simulated signals.

9. The method according to claim 8, further comprising correcting the defect by using the at least one electron beam.

10. The method of claim 9, wherein the defect is a defect of a multi-layer structure of the photolithographic mask which is repaired by a compensational repair of an absorber layer of the photolithographic mask.

11. The method according to claim 9, further comprising determining the performance of the repaired portion of the photolithographic mask at the predetermined exposure wavelength.

12. An apparatus for predicting a performance of a photolithographic mask at a predetermined exposure wavelength, comprising:
   a. at least one electron source for generating at least one electron beam, wherein the at least one electron source is operable to generate electron beams with multiple energies, and wherein the performance of a photolithographic mask is defined by its capability to transmit a predetermined structure or pattern in a photoresist arranged on a wafer;
   b. at least one adjusting means for repeatedly scanning the at least one electron beam with multiple beam energies across the at least one portion of the photolithographic mask;
   c. at least one detector for measuring signals generated by the at least one electron beam interacting with the at least one portion of the photolithographic mask, wherein if the photolithographic mask includes a defect, the signals include positional information on the defect; and
   d. at least one computing means for determining whether the defect is a defect of an absorber layer of the photolithographic mask or a defect of a multilayer structure of the photolithographic mask, and, if the defect is a defect of the multi-layer structure of the photolithographic mask, predicting the performance of the at least one portion of the photolithographic mask at the predetermined exposure wavelength based on the measured signals, and determining whether a repair of the defect is required based on a discrepancy between the determined performance and a predetermined performance.

13. The apparatus according to claim 12, further comprising at least one means for providing at least one precursor gas at a position the electron beam hits the photolithographic mask.

14. The method of claim 2 in which the photolithographic mask comprises a photolithographic mask for an extreme ultraviolet (EUV) exposure wavelength.

15. The method of claim 2 in which measuring signals comprises measuring backscattered electrons and wherein measuring backscattered electrons comprises at least one of measuring a yield of backscattered electrons or measuring an energy distribution of backscattered electrons.

16. The method of claim 2 in which measuring signals comprises measuring photons using energy dispersive x-ray spectroscopy (EDX).

17. The method according to claim 2, wherein measuring signals comprises measuring electrons and measuring photons.

18. The method according to claim 2, further comprising simulating signals generated by the electron beam interacting with the portion of the photolithographic mask and determining the performance of the portion of the photolithographic mask at the predetermined exposure wavelength evaluating simulated and measured signals.

19. The method according to claim 2, further comprising determining a defect in the performance at the predetermined exposure wavelength of a portion of the photolithographic mask by evaluating measured signals of a portion of the photolithographic mask and/or by evaluating measured and simulated signals.

20. The method of claim 3 in which measuring signals comprises measuring backscattered electrons and wherein measuring backscattered electrons comprises at least one of measuring a yield of backscattered electrons or measuring an energy distribution of backscattered electrons.

21. The method of claim 17, wherein measuring electrons and measuring photons comprise measuring backscattered electrons and measuring photons using energy dispersive x-ray spectroscopy.

* * * * *